(12) United States Patent
Wang et al.

(10) Patent No.: US 9,453,801 B2
(45) Date of Patent: Sep. 27, 2016

(54) PHOTOEMISSION MONITORING OF EUV MIRROR AND MASK SURFACE CONTAMINATION IN ACTINIC EUV SYSTEMS

(71) Applicant: KLA-Tencor Corporation, Milpitas, CA (US)

(72) Inventors: Li Wang, San Ramon, CA (US); Daimian Wang, Fremont, CA (US); Yanwei Liu, Danville, CA (US); Alan Michael Aindow, Alameda, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 260 days.

(21) Appl. No.: 13/898,705

(22) Filed: May 21, 2013

(65) Prior Publication Data

US 2013/0313442 A1     Nov. 28, 2013

Related U.S. Application Data

(60) Provisional application No. 61/651,863, filed on May 25, 2012, provisional application No. 61/651,876, filed on May 25, 2012.

(51) Int. Cl.
*G01N 21/956* (2006.01)
*G01N 21/94* (2006.01)
(Continued)

(52) U.S. Cl.
CPC ............ *G01N 21/956* (2013.01); *G01N 21/94* (2013.01); *G03F 1/86* (2013.01); *G06T 7/0004* (2013.01);
(Continued)

(58) Field of Classification Search
CPC ................. G06T 7/0004; G01N 21/88–21/96

USPC ......................................................... 250/395
See application file for complete search history.

(56) References Cited

U.S. PATENT DOCUMENTS 4,748,327 A * 5/1988 Shinozaki ................. G03F 1/86
250/358.1
4,776,693 A * 10/1988 Imamura ................ G01N 21/94
356/237.3
(Continued)

FOREIGN PATENT DOCUMENTS

EP          2423749           2/2012
JP      H4-274793 A  *  9/1992    ............... G01T 1/20
(Continued)

OTHER PUBLICATIONS

International Search Report and Written Opinion from PCT/US2013/042548, dated Sep. 25, 2013, KLA-Tencor Corporation, pp. 1-12.
(Continued)

*Primary Examiner* — David Porta
*Assistant Examiner* — Jeremy S Valentiner
(74) *Attorney, Agent, or Firm* — Meyertons, Hood, Kivlin, Kowert & Goetzel, P.C.; Eric B. Meyertons

(57) ABSTRACT

Photoelectron emission mapping systems for use with EUV (extreme ultraviolet) mask inspection and lithography systems are described. The mapping systems may be used to provide photoelectron emission maps for EUV photolithography masks and/or EUV mirrors. The systems use EUV photoelectron sources used for mask inspection or photolithography to impinge EUV light on the masks and/or mirrors. The EUV light generates photoelectron on the surfaces of the mask and/or mirrors and the photoelectrons are collected and analyzed by detectors placed away from optical spaces of the EUV chamber.

18 Claims, 2 Drawing Sheets

(51) Int. Cl.
  *G03F 1/86* (2012.01)
  *H01L 31/0216* (2014.01)
  *G06T 7/00* (2006.01)
  *G01N 23/227* (2006.01)

(52) U.S. Cl.
  CPC ..... *H01L 31/02168* (2013.01); *G01N 23/2273* (2013.01); *G01N 2223/611* (2013.01); *G01N 2223/652* (2013.01)

(56) References Cited

U.S. PATENT DOCUMENTS

| | | | |
|---|---|---|---|
| 4,998,019 A * | 3/1991 | Stokowski | G01N 23/227 250/358.1 |
| 5,508,528 A | 4/1996 | Mulkens et al. | |
| 6,038,015 A * | 3/2000 | Kawata | B82Y 10/00 134/1 |
| 6,184,686 B1 | 2/2001 | Mazor et al. | |
| 6,545,272 B1 * | 4/2003 | Kondo | G01N 22/00 250/305 |
| 6,710,351 B2 | 3/2004 | Berger | |
| 6,774,990 B2 | 8/2004 | Liang et al. | |
| 6,842,500 B1 | 1/2005 | Komatsuda et al. | |
| 6,847,463 B2 | 1/2005 | Malinowski | |
| 6,987,278 B2 | 1/2006 | Loopstra | |
| 7,060,993 B2 | 6/2006 | Wedowski et al. | |
| 7,107,158 B2 | 9/2006 | Steele et al. | |
| 7,136,142 B2 | 11/2006 | Beckers et al. | |
| 7,365,324 B2 | 4/2008 | Noji et al. | |
| 7,375,791 B2 | 5/2008 | Vogel et al. | |
| 7,405,417 B2 | 7/2008 | Stevens et al. | |
| 7,432,513 B2 | 10/2008 | Van Empel et al. | |
| 7,449,704 B2 | 11/2008 | Fomenkov et al. | |
| 7,473,916 B2 | 1/2009 | Singh | |
| 7,486,392 B2 | 2/2009 | Yang et al. | |
| 7,599,048 B2 | 10/2009 | Yoo et al. | |
| 7,900,526 B2 | 3/2011 | Hawthorne et al. | |
| 7,928,412 B2 | 4/2011 | Van Herpen et al. | |
| 7,952,071 B2 | 5/2011 | Noji et al. | |
| 8,054,446 B2 | 11/2011 | Kraus et al. | |
| 2002/0034325 A1 * | 3/2002 | Reinhorn | G01N 21/95692 382/145 |
| 2002/0190642 A1 | 12/2002 | Berger et al. | |
| 2004/0011381 A1 | 1/2004 | Klebanoff et al. | |
| 2004/0227102 A1 | 11/2004 | Kurt et al. | |
| 2005/0121611 A1 * | 6/2005 | Kimba | G01N 23/225 250/311 |
| 2005/0214958 A1 * | 9/2005 | Nakasuji | G01N 23/225 438/14 |
| 2007/0008517 A1 | 1/2007 | Fomenkov et al. | |
| 2007/0139646 A1 * | 6/2007 | Singh | 356/237.2 |
| 2007/0139648 A1 * | 6/2007 | Singh | 356/337 |
| 2007/0285643 A1 | 12/2007 | Wedowski et al. | |
| 2008/0315134 A1 | 12/2008 | Ehm et al. | |
| 2009/0059196 A1 | 3/2009 | Bakshi et al. | |
| 2009/0224151 A1 | 9/2009 | Hatakeyama et al. | |
| 2010/0149505 A1 * | 6/2010 | Sewell et al. | 355/67 |
| 2010/0208978 A1 | 8/2010 | Terasawa et al. | |
| 2010/0237243 A1 * | 9/2010 | Noji et al. | 250/310 |
| 2011/0231134 A1 | 9/2011 | Yoshitake | |
| 2012/0045855 A1 | 2/2012 | Beck et al. | |
| 2013/0054153 A1 * | 2/2013 | Motl | H01J 37/222 702/28 |

FOREIGN PATENT DOCUMENTS

| | | |
|---|---|---|
| KR | 2010-0078311 | 7/2010 |
| WO | WO02065213 | 8/2002 |
| WO | WO2009025557 | 2/2009 |

OTHER PUBLICATIONS

"Lithography and Other Patterning Techniques for Future Electronics" Downloaded from ieeexplore.ieee.org/ieee_pilot/articles/96jproc02/96jproc02-pease/article.html, pp. 1-23.

"Low-energy electron bombardment induced surface contamination of Ru mirrors" A.B.A. Al-Ajlony, et al, 2012, pp. 18-19.

"Surface Phenomena Related to Mirror Degradation in Extreme Ultraviolet (EUV) Lithography" Theodore E Madey, et al. Published Jul. 10, 2006, pp. 1-18.

"Impact: A Facility to Study the Interaction of Low-energy Intense Particle Beams with Dynamic Heterogeneous Surfaces" JP Allain, et al, American Institute of Physics 2007, pp. 1-14.

"Resonance Effects in Photoemission from $TiO_2$-Capped Mo/Si Multilayer Mirrors for Extreme Ultraviolet Applications" Nadir S. Faradzhev, et al, American Institute of Physics 2011, pp. 1-8.

Neuhausler, et al "A New Approach for Actinic Defect Inspection of EUVL Multilayer Mask Blanks: Standing Wave Photoemission Electron Microscopy" Microelectronic Engineering, vol. 83, issues 4-9, Apr.-Sep. 2006, pp. 680-683.

Juequan Chen, et al "Secondary electron yield measurements of carbon covered multilayer optics", 2010, p. 1.

"Cleaning Contaminants from EUV Mirrors" Mar. 2, 2005, pp. 1-2.

"Characterization of EUV induced carbon films using laser-generated surface acoustic waves" Diamond and related materials, vol. 18, issues 5-8, May-Aug. 2009, pp. 768-771.

* cited by examiner

PHOTOEMISSION MONITORING OF EUV MIRROR AND MASK SURFACE CONTAMINATION IN ACTINIC EUV SYSTEMS

PRIORITY CLAIM

This patent claims priority to U.S. Provisional Patent Application No. 61/651,863 filed May 25, 2012 and U.S. Provisional Patent Application No. 61/651,876 filed May 25, 2012, both of which are incorporated by reference in their entirety.

BACKGROUND

1. Field of the Invention

The present invention relates to surface contamination detection. More particularly, the invention relates to photoemission detection of surface contamination on mirrors or masks used in EUV (extreme ultraviolet) technology.

2. Description of Related Art

U.S. Pat. No. 4,998,019 to Stokowski et al., which is incorporated by reference as if fully set forth herein, describes contaminant detection on the surface of a variety of electrically conductive materials (e.g., semiconductor surfaces, metals, or metal silicides). FIGS. 1 and 2 depict an example of a photocontamination detection scheme using UV light source (15, 35), focusing optics (17,37), and set of electrodes (41) to pick up photoemission from the test surface. Positive bias supplies (43, 50) and set of electrodes (49) provide correction for capacitive changes with gap dimension. Operational amplifiers (45, 52), differential processing (55), and a mechanical scan method (13) allow coverage of all points on the test surface.

The photocontamination detection scheme disclosed in U.S. Pat. No. 4,998,019 is intended for use at pressures up to atmospheric pressure with the electrodes running close to the test surface to minimize electron attachment and loss of sensitivity (mainly due to $O_2$ presence). Electron attachment and the loss of sensitivity could also be minimized by introducing gases such as He, Ne, Ar, Kr, Xe, or $N_2$ into the optional electrical shield (59). The disclosed scheme may be very sensitive with the photoelectric current being reduced by up to four to six orders of magnitude by an increase in the contamination layer thickness of 100 Å. The disclosed scheme is a stand alone test, however, that requires a dedicated UV light source and close location of the electrodes to the test surface in order to maintain sensitivity. The close location of the electrodes may interfere with the primary EUV beam path and may require the second set of electrodes to compensate for capacitance gap-related changes, which increases the design complexity of the system.

Several techniques for contamination detection using photoelectric emission detection have been subsequently developed for EUV lithography (EUVL). These techniques can be used to not only monitor contamination and radiation flux but to also maintain system optical alignment, control EUVL exposure levels, and regulate cleaning processes. Examples of these techniques may be found in U.S. Pat. Appl. Pub. Nos. 2002/0190642; 2007/0008517; and 2009/0059196; and U.S. Pat. Nos. 6,710,351; 6,545,272; 6,842,500; 7,060,993; and 7,928,412, all of which are incorporated by reference as if fully set forth herein. Some problems with these techniques include invasive features such as requiring electrically isolated and biased EUVL mirrors with surface contact or employing detectors built into the structure of ML (multilayered) mirrors. Other problems include constraints in the space envelope with arranged detectors at pre-defined angles to the target, unknown/unspecified sensitivities due to using unspecified ammeters to monitor photoelectric currents, required structure and support by using electrodes in forms of rings directly above mirrors to monitor photoelectric currents, required gas supplies and regulation by introducing gases into the EUV vacuum system to emit photoelectrons in situ along the EUV path, and/or having unspecified detectors and unidentified means of coupling radiation or photoelectrons.

Many other techniques have also been used for detecting surface contaminants including, but not limited to, other forms of photoemission spectroscopy (e.g., angle-resolved photoemission spectroscopy (ARPES)), X-ray photoelectron spectroscopy (XPS), time-of-flight secondary ion mass spectrometry (TOF-SIMS), and Auger electron spectroscopy (AES). Such techniques are capable of detecting surface contaminants at extremely low levels. These techniques, however can be costly, have conflicting space envelope issues, have a large footprint, cause surface damage, and/or be difficult to integrate into EUV mask inspection systems. The conflicting space envelope issues arises due to many of the surface contamination detection systems not being able to easily fit into the space envelope of EUV mask inspection systems. Additionally, drive, source, control, and other ancillary equipment may require considerable additional footprint.

SUMMARY

In certain embodiments, a photoelectron emission mapping system for photolithography masks includes a mask defect inspection stage, a photoelectron source (e.g., an EUV light source) used for mask inspection, and a photoelectron detector located outside a beam path between the photoelectron source and the mask defect inspection stage. The photoelectron detector may detect photoelectrons emitted from a surface of a mask (e.g., an EUV photolithography mask) coupled to the mask defect inspection stage when light from the photoelectron source impinges on the mask during inspection of the mask. The surface of the mask may be biased at a lower voltage than a region around the photoelectron detector during use. In some embodiments, fiber optics are used to introduce a time delay between emission of light from the photoelectron source and detection of photoelectrons by the photoelectron detector. The photoelectron detector may detect both intensity and electron spectrum of the photoelectrons emitted from the mask surface. The system may assess both photoelectron dose and contamination at the surface of the mask.

In certain embodiments, a method for assessing contamination on one or more photolithography masks includes providing a photolithography mask to a mask defect inspection stage and providing an inspection beam of light to the mask from a photoelectron source. Photoelectrons emitted from a surface of the mask may be collected using a photoelectron detector. The photoelectrons may be created by impingement of the inspection beam on the surface of the mask. The photoelectron detector is located outside a path of the inspection beam between the photoelectron source and the mask defect inspection stage. One or more properties of the photoelectrons may be assessed to provide a photoelectron emission map of the surface of the mask.

In certain embodiments, a photoelectron emission mapping system for extreme ultraviolet (EUV) mirrors includes an EUV mirror, an EUV photoelectron source, and a photoelectron detector located to the side of the mirror. The photoelectron detector may detect photoelectrons emitted from a surface of the mirror when light from the photoelectron source impinges on the mirror. The surface of the mirror may be biased at a lower voltage than a region around the photoelectron detector. Fiber optics may be used to introduce a time delay between emission of light from the photoelectron source and detection of photoelectrons by the photoelectron detector. In some embodiments, the photoelectron detector includes a scintillator, a light pipe, and a photoelectron multiplier tube. The scintillator may have a voltage larger than a voltage at the surface of the mirror during use to accelerate photoelectrons towards the scintillator.

In certain embodiments, a method for assessing contamination on one or more extreme ultraviolet (EUV) mirrors includes providing a beam of EUV light to an EUV mirror from a photoelectron source and collecting photoelectrons emitted from a surface of the mirror using a photoelectron detector. The photoelectrons may be created by impingement of the EUV beam on the surface of the mirror. The photoelectron detector may be located to the side of the mirror. One or more properties of the photoelectrons may be assessed to provide a photoelectron emission map of the surface of the mirror. In some embodiments, both intensity and electron spectrum of the photoelectrons emitted from the mask surface are assessed. In some embodiments, radiation dose and contamination on the mirror are assessed using the assessed properties of the photoelectrons.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which.

Figure 1:
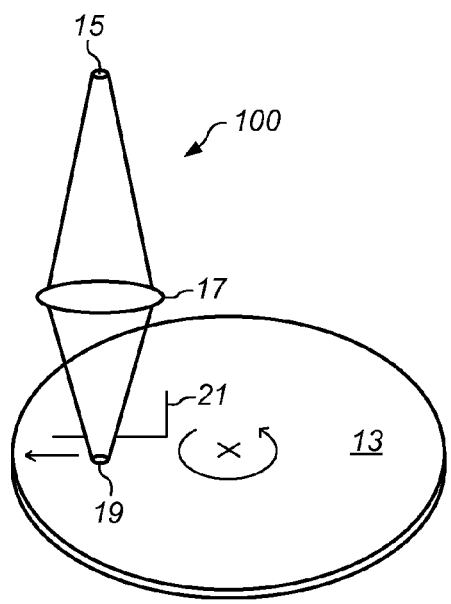
FIGS. 1 and 2 depict a prior art example of a photocontamination detection scheme.
Figure 2:
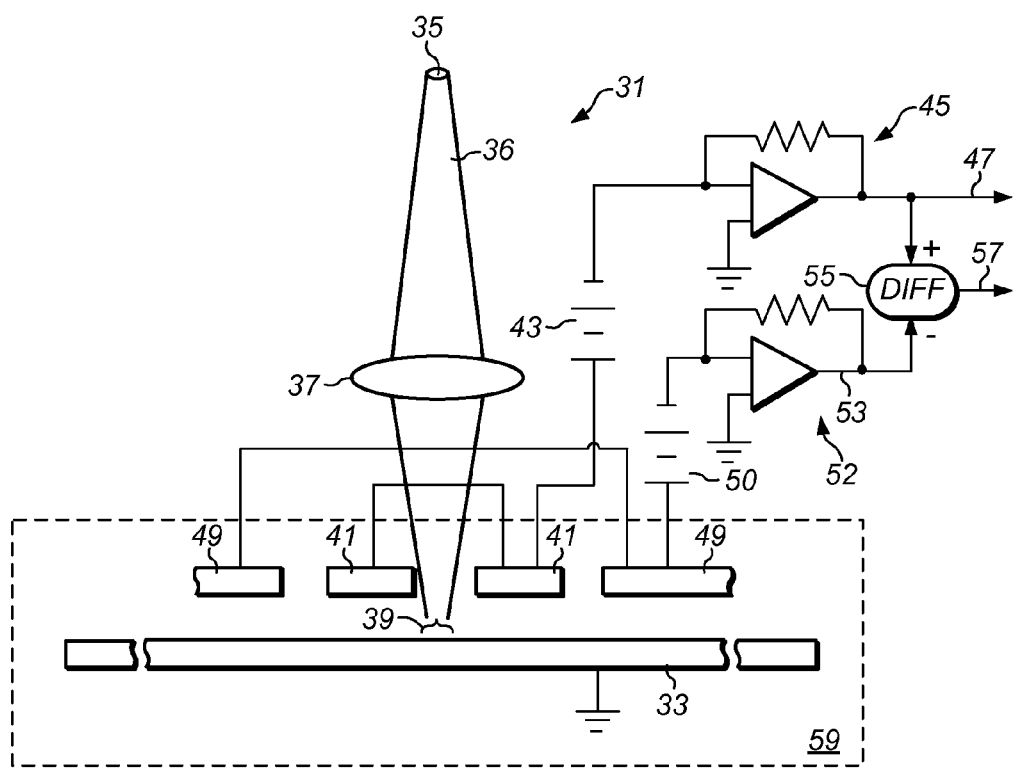

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION OF EMBODIMENTS

In the context of this patent, the term "coupled" means either a direct connection or an indirect connection (e.g., one or more intervening connections) between one or more objects or components. The phrase "directly connected" means a direct connection between objects or components such that the objects or components are connected directly to each other so that the objects or components operate in a "point of use" manner.

Figure 3:
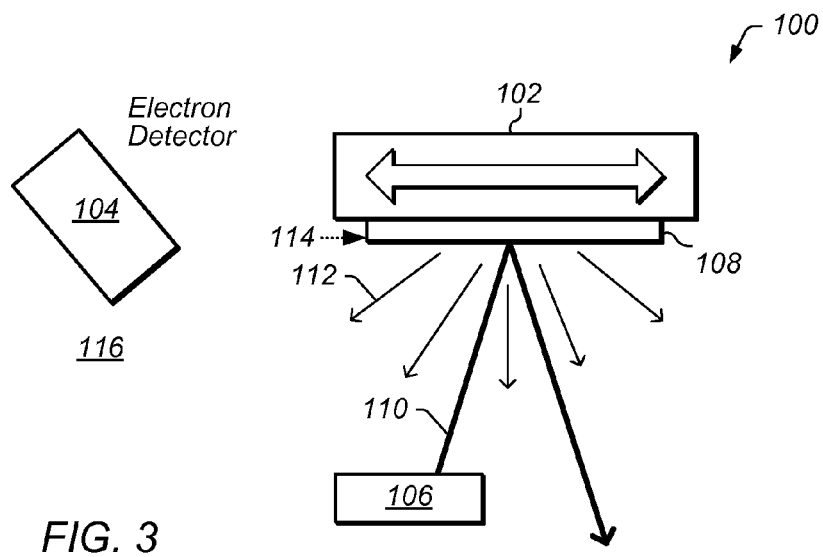
FIG. 3 depicts a schematic of an embodiment of a photoelectron emission mapping system.

FIG. 3 depicts a schematic of an embodiment of photoelectron emission mapping system 100. System 100 may be used to provide a map of photelectron emission on a test surface (e.g., an EUV photolithography mask). System 100 may be located in a vacuum chamber (e.g., an EUV chamber). The photoelectron emission map may be used as an indicator of surface property changes and/or dosed radiation on the EUV mask. Surface property changes may be caused by, for example, contamination that may lead to photoelectron yield change. In certain embodiments, system 100 provides the photoelectron emission map in real-time (e.g., in situ) during EUV mask inspection. In some embodiments, system 100 provides the photoelectron emission map during a separate diagnostic procedure.

In certain embodiments, system 100 includes mask defect inspection stage 102, detector 104, and photoelectron source 106. Mask 108 may be coupled to mask defect inspection stage 102. Mask 108 may be, for example, an EUV photolithography mask or other photolithography mask. In certain embodiments, mask defect inspection stage 102 and photoelectron source 106 are part of an actinic EUV mask defect inspection system. For example, mask 108 may be inspected for defects at mask defect inspection stage 102 using EUV provided by photoelectron source 106. In some embodiments, mask defect inspection stage 102 is coupled to other systems for transferring or transporting masks to/from the mask defect inspection stage.

In certain embodiments, photoelectron source 106 is an EUV light source. For example, photoelectron source 106 may provide light at wavelengths between about 5 nm and about 124 nm (the EUV wavelength range). EUV beam 110 from photoelectron source 106 may be used for defect inspection of mask 108.

In certain embodiments, detector 104 is located at the side of mask defect inspection stage 102 (e.g., out of the path of EUV from photoelectron source 106 or the optics space envelopes in system 100). Detector 104 may be a photoelectron detector. For example, detector 104 may be used to detect photoelectrons ejected from mask 108 during exposure to EUV beam 110 from photoelectron source 106. Detector 104 may be any photoelectron detector capable of detecting photoelectrons at the sensitivity and bandwidth limits needed in system 100. Examples of detectors suitable for use as detector 104 include, but are not limited to, a scintillator-light pipe-PMT (photoelectron multiplier tube) combination detector, a scintillator-APD (avalanche photodiode) detector, an electron multiplier detector, an MCP (microchannel plate) detector, or a biased electrode detector. In some embodiments, multi-pixel photon counting (MCCP) devices based upon single photon APD arrays may be used instead of a PMT or linear APD array.

During exposure to EUV beam 110 from photoelectron source 106, photons from EUV beam 110 are absorbed in the surface of mask 108 and create photoelectrons 112 that emit from the mask surface. The yield rate of photoelectrons 112 may depend on the binding energy of the particular material of the surface of mask 108 that interacts with EUV photons from EUV beam 110. The photoelectron yield will vary based on the contamination on the surface of mask 108. For example, the photoelectron yield may vary based on carbon deposition or oxidation on the surface of mask 108. Thus, detection of the photoelectron yield using detector 104 may provide information on the surface contamination level or other surface property changes of mask 108.

In certain embodiments, detector 104 detects (e.g., collects) photoelectrons 112 that emit from mask 108 (e.g., the surface of the mask) during EUV exposure (e.g., during EUV exposure used to inspect the mask). The collected photoelectrons may be analyzed and assessed to provide a photoelectron emission map of the surface of mask 108. EUV beam 110 may have a finite spot size on the surface of mask 108 during scanning of the mask surface. In some embodiments, EUV beam 110 scans the surface of mask 108 in a serial fashion (as shown by the arrows in FIG. 3). In certain embodiments, detector 104 assesses both intensity and electron spectra of photoelectrons 112 as related to radiation dose, contamination levels, and contamination species. Thus, both EUV dose and contamination at the surface of mask 108 may be assessed using system 100 (e.g., the photoelectron emission map includes data on both EUV dose and contamination at the surface of the mask).

In certain embodiments, voltage 114 at the surface of mask 108 is biased lower than voltage 116 in the region of detector 104. Biasing voltage 114 lower than voltage 116 may increase electron collection efficiency in detector 104. In some embodiments, voltage 114 at mask 108 is given a negative potential relative to voltage 116. Providing the negative potential may inhibit photoelectron return to mask 108.

After EUV beam 110 finishes a scan of a selected area on mask 108, a signal history log of photoelectrons 112 detected at detector 104 may be recorded. The signal history log may provide a photoelectron emission (capability) map of the surface of mask 108 at the point in time of the scan. The spatial resolution of the photoelectron emission map may be limited by the size of EUV beam 110. For example, if the spot size of EUV beam 110 on the mask is about 0.5 mm×0.5 mm, the photoelectron emission map may have a comparable spatial resolution. In some embodiments, the photoelectron emission map is created during a time interval in which a surface property of mask 108 changes. If such a change occurs, the photoelectron emission capability map may show (e.g., reveal) the surface property change.

In certain embodiments, if detector 104 is a scintillator-light pipe-PMT (photoelectron multiplier tube) combination detector or a scintillator-APD (avalanche photodiode) detector, fiber optics are used in detector 104 to introduce a time delay between pulse emission from the source and data collections at detector 104. The fiber optics may be placed between the scintillator, where visible light is generated by photoelectrons, and the PMT or APD detectors. Introducing the time delay may temporally separate the electromagnetic noise from photoelectron source 106 at detector 104 and the optical signal generated by the photoelectrons from the mask, thus, increasing signal-to-noise ratios at detector 104.

In some embodiments, system 100 includes one or more accelerating electrodes positioned at or near detector 104. The accelerating electrodes may be biased at positive potential to attract electrons towards detector 104. In some embodiments, system 100 includes one or more imaging electrodes and one or more detectors used for sub-patch photoemission electron microscopy (PEEM).

In certain embodiments, system 100 includes one or more electron intensity and spectrum analyzers. The analyzers may be placed in or near the photoelectron collection (detection) path. The analyzers may be used to assess both the electron intensity and spectrum of photoelectrons 112. Analyzing both the electron intensity and spectrum of photoelectrons 112 may be used to provide assessment of both dose and contamination on mask 108. The spectrum analyzers may be based on, for example, magnetic-field induced electron trajectory bending, time-of-flight, or stopping-potential discrimination. In some embodiments, the analyzers are based on filtering for compactness, simplicity, and low cost. The filtering may be a mosaic of differing thickness of absorber placed in front of a very thin scintillator positioned on top of a CCD camera or APD array. Thus, cumulative electron spectra may be assessed with a single detector array similar to Auger spectra of contaminants on surfaces.

System 100 may provide a system for mask contamination detection in situ (e.g., in real time) with EUV mask inspection. Detector 104 allows in situ detection of photoelectrons emitted from the surface of mask 108 during impingement of the EUV mask inspection beam. Thus, no secondary sources of radiation are needed to generate photoelectrons for detection by detector 104. Detection of photoelectrons 112 may be non-invasive as there is no interference with the path of EUV beam 110 or optics spaces by detector 104. Detection of photoelectrons 112 using detector 104 may provide a sensitive method for detecting trace concentrations of contaminants on the mask surface. In certain embodiments, a yield of photoelectrons on the order of $10^9$ are generated with each pulse from EUV beam 110. Such a yield should provide enough signal level of photoelectrons for high sensitivity detection using detector 104.

Generating photoelectrons 112 using EUV beam 110 provides no surface or localized damage to mask 108. Thus, system 100 provides a non-destructive system for assessment of surface contamination unlike, for example, TOF-SIMS. Because system 100 may be integrated into an existing mask inspection system, system 100 provides a low cost implementation for detecting and characterizing contamination on mask surfaces.

In some embodiments, system 100 is used to provide a stand alone diagnostic procedure for masks (e.g. tooling masks). For example, system 100 may be used for diagnostic procedures performed independently of any mask inspection. In some embodiments, system 100 is used to detect contamination on a pellicle used near the top of a mask. The pellicle may be a thin film applied near the top of the mask to block particles from falling onto the mask. When using the pellicle, system 100 may be used to detect contamination on the pellicle. Use of the pellicle may, however, disable or inhibit detection of contamination on the mask.

Figure 4:
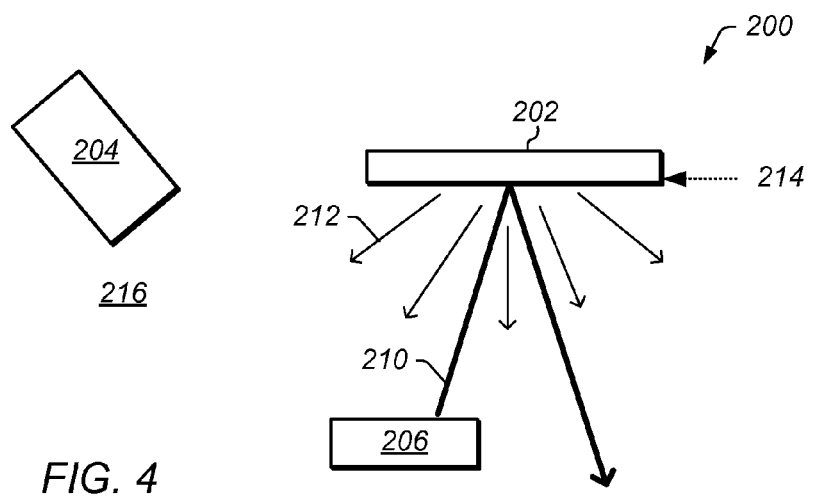
FIG. 4 depicts a schematic of another embodiment of a photoelectron emission mapping system.

FIG. 4 depicts a schematic of an embodiment of photoelectron emission mapping system 200. System 200 may be used to provide a map of photoelectron emission on mirror surfaces (e.g., mirrors used in EUV technology). System 200 may be located in a vacuum chamber (e.g., an EUV chamber). The photoelectron emission map may be used as an indicator of surface property changes and/or absorbed radiation doses on the EUV mirror. Surface property changes may be caused by, for example, contamination due to carbon deposition or oxidation on the surface of the mirror and/or particulation issues during EUV lithography or inspection operations. System 200 may provide assessment of total photoelectric yield from the mirror in relation to factors such as, but not limited to, radiation dose and contaminant thickness. System 200 may provide assessment of photoelectron energy from the mirror in relation to factors such as, but not limited to, contaminant species.

In certain embodiments, system 200 includes mirror 202, detector 204, and photoelectron source 206. Mirror 202 may be placed or held in place for testing using techniques known in the art. Mirror 202 may be a mirror used in EUV technology. For example, mirror 202 may be a normal incidence mirror having Mo/Si multilayers with or without a Ru (ruthenium) cap layer or mirror 202 may be a grazing angle incident mirror with Ru coating.

In certain embodiments, photoelectron source 206 is an EUV light source. For example, photoelectron source 206 may provide light at wavelengths between about 10 nm and about 124 nm (the EUV wavelength range). EUV beam 210 from photoelectron source 206 may impinge (be incident on) mirror 202.

In certain embodiments, detector 204 is located at the side of mirror 202 (e.g., out of the path of EUV beam 210 from photoelectron source 202 or the optics space envelopes in system 200). Detector 204 may be a photoelectron detector. For example, detector 204 may be used to detect photoelectrons ejected from mirror 202 during exposure to EUV beam 210 from photoelectron source 206. Detector 204 may be any photoelectron detector capable of detecting photoelectrons at the sensitivity and bandwidth limits needed in system 200. Examples of detectors suitable for use as detector 204 include, but are not limited to, a scintillator-light pipe-PMT combination detector (shown in FIG. 5), a scintillator-APD detector, an electron multiplier detector, an MCP detector, or a biased electrode detector. In some embodiments, multi-pixel photon counting (MCCP) devices based upon single photon APD arrays may be used instead of a PMT or linear APD array.

During exposure to EUV beam 210 from photoelectron source 206, photons from EUV beam 210 are absorbed in the surface of mirror 202 and create photoelectrons 212 that emit from the mirror surface. The yield rate of photoelectrons 212 may depend on the binding energy of the particular material of the surface of mirror 202 that interacts with EUV photons from EUV beam 210. The photoelectron yield will vary based on the contamination on the surface of mirror 202. For example, the photoelectron yield may vary based on carbon deposition or oxidation on the surface of mirror 202. Thus, detection of the photoelectron yield using detector 204 may provide information on the surface contamination level or other surface property changes of mirror 202.

In certain embodiments, detector 204 detects (e.g., collects) photoelectrons 212 that emit from mirror 202 (e.g., the surface of the mirror) during EUV exposure. The collected photoelectrons may be analyzed and assessed to provide a photoelectron emission map of the surface of mirror 202. EUV beam 210 may have a finite spot size on the surface of mirror 202 during scanning of the mirror surface. In some embodiments, EUV beam 210 scans the surface of mirror 202 in a serial fashion. In certain embodiments, detector 204 assesses both intensity and electron spectra of photoelectrons 212 as related to radiation dose, contamination levels, and contamination species. Thus, both EUV dose and contamination at the surface of mirror 202 may be assessed using system 200 (e.g., the photoelectron emission map includes data on both EUV dose and contamination at the surface of the mirror).

In certain embodiments, voltage 214 at the surface of mirror 202 is biased lower than voltage 216 in the region of detector 204. Biasing voltage 214 lower than voltage 216 may increase electron collection efficiency in detector 204. Biasing of the voltages to increase electron collection efficiency may provide high detection rates and high contamination sensitivity in system 200. In certain embodiments, detector 204 is placed at a selected distance away from photoelectron source 206 that inhibits mechanical interference with the photoelectron source. Detector 204 may be placed at the selected distance as long as voltage 216 is sufficiently large compared to voltage 214 to still attract electrons to the detector front surface for collection and/or amplification.

After EUV beam 210 finishes a scan of a selected area on mirror 202, a signal history log of photoelectrons 212 detected at detector 204 may be recorded. The signal history log may provide a photoelectron emission (capability) map of the surface of mirror 202 at the point in time of the scan. The spatial resolution of the photoelectron emission map may be limited by the size of EUV beam 210, as described above for EUV beam 110. In some embodiments, the photoelectron emission map is created during a time interval in which a surface property of mirror 202 changes. If such a change occurs, the photoelectron emission capability map may show the surface property change.

Figure 5:
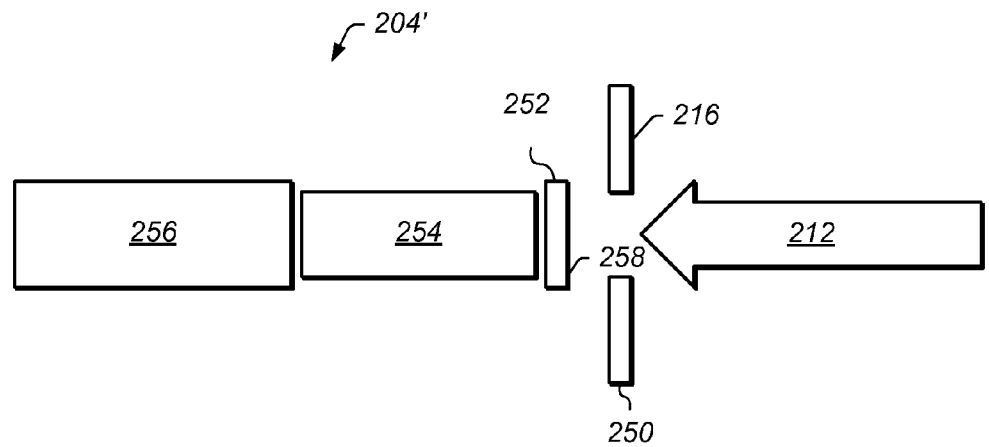
FIG. 5 depicts a schematic of an embodiment of a modified Everhart-Thornley type detector.

In certain embodiments, detector 204 is an Everhart-Thornley type detector (e.g., a type of scintillator-light pipe-PMT combination detector). FIG. 5 depicts a schematic of an embodiment of a modified Everhart-Thornley type detector 204'. Detector 204' includes biasing electrode 250 in front of scintillator 252, which is followed by light pipe 254 and photoelectron multiplier tube (PMT) 256. For collection of photoelectrons 212, voltage 216 at biasing electrode 250 needs to be sufficiently larger than voltage 214 at mirror 202 (shown in FIG. 4) to attract photoelectrons to the area of scintillator 252. Additionally, voltage 258 at scintillator 252 needs to be larger than voltage 216 to accelerate the photoelectrons to have enough energy to create electrons on the scintillator. PMT 256 may amplify the electron signal to provide a desired signal level.

It may be possible to use other detectors to provide similar functions to detector 204'. For example, another embodiment of detector 204 may include a Marketech type very thin wafer scintillator coupled to a fiber optic cable that is routed to an avalanche photodiode (APD). The APD may be mounted remotely (e.g., outside the EUV chamber). The fiber optic cable (or any other fiber optics used in system 200) may be used to introduce a time delay between pulse emission from photoelectron source 206 and data collections at detector 204. Introducing the time delay may temporally separate the electromagnetic noise from photoelectron source 206 at the detector and the optical signal generated by the photoelectrons from the mirror, thus increasing signal-to-noise ratios at detector 204.

In certain embodiments, system 200 includes one or more electron intensity and spectrum analyzers. The analyzers may be placed in or near the photoelectron collection (detection) path. The analyzers may be used to assess both the electron intensity and spectrum of photoelectrons 212. Analyzing both the electron intensity and spectrum of photoelectrons 212 may be used to provide assessment of both dose and contamination on mirror 202. The spectrum analyzers may be based on, for example, magnetic-field induced electron trajectory bending, time-of-flight, or stopping-potential discrimination. In some embodiments, the analyzers are based on filtering for compactness, simplicity, and low cost. The filtering may be a mosaic of differing thickness of absorber placed in front of a very thin scintillator positioned on top of a CCD camera or APD array. Thus, cumulative electron spectra may be assessed with a single detector array similar to Auger spectra of contaminants on surfaces.

System 200 may provide a system for contamination detection in situ (e.g., in real time) for mirrors used in EUV mask inspection and lithography systems. Detector 204 allows in situ detection of photoelectrons emitted from the surface of mirror 202 during impingement of EUV beam 210. Thus, no secondary sources of radiation are needed to generate photoelectrons for detection by detector 204 as the source of radiation is a commonly used radiation source in EUV systems. Detection of photoelectrons 212 may be non-invasive as there is no interference with the path of EUV beam 210 or optics spaces by detector 204. Detection of photoelectrons 212 using detector 204 may provide a sensitive method for detecting trace concentrations of contaminants on the mask surface.

Generating photoelectrons 212 using EUV beam 210 provides no surface or localized damage to mirror 202. Thus, system 200 provides a non-destructive system for assessment of surface contamination unlike, for example, TOF-SIMS. Because system 200 may be integrated into an existing mask inspection or lithography system, system 200 provides a low footprint, low cost implementation for detecting and characterizing contamination on EUV mirror surfaces. In some embodiments, system 200 is used to provide a stand-alone diagnostic procedure for EUV mirrors. For example, system 200 may be used for diagnostic procedures performed independently of any mask inspection or lithography system.

It is to be understood the invention is not limited to particular systems described which may, of course, vary. It is also to be understood that the terminology used herein is for the purpose of describing particular embodiments only, and is not intended to be limiting. As used in this specification, the singular forms "a", "an" and "the" include plural referents unless the content clearly indicates otherwise. Thus, for example, reference to "a source" includes a combination of two or more sources and reference to "a contaminant" includes mixtures of contaminants.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A photoelectron emission mapping system for photolithography masks, comprising:
    a mask defect inspection stage;
    a photoelectron source used for mask inspection;
    a photoelectron detector located outside a beam path between the photoelectron source and the mask defect inspection stage, the photoelectron detector comprising a scintillator, wherein the photoelectron detector is configured to detect photoelectrons emitted from a surface of a mask coupled to the mask defect inspection stage when light from the photoelectron source impinges on the mask during inspection of the mask, and wherein the photoelectron detector is configured to assess both electron intensity and electron spectra of the photoelectrons emitted from the surface of the mask, the photoelectron detector comprising a processor configured to assess radiation dose, contamination level, and contamination species on the mask using the assessed electron intensity and electron spectra of the photoelectrons; and
    a biasing electrode located between the mask and the scintillator;
    wherein the surface of the mask is biased at a first voltage during use and the biasing electrode is biased at a second voltage during use, wherein the second voltage is a positive potential, and wherein the first voltage has a negative potential relative to the second voltage.

2. The system of claim 1, wherein the photoelectron detector is located a distance from the photoelectron source that inhibits the photoelectron detector causing mechanical interference with the photoelectron source.

3. The system of claim 1, further comprising fiber optics located between the photoelectron source and the photoelectron detector, wherein the fiber optics are used to introduce a time delay between emission of light from the photoelectron source and detection of photoelectrons by the photoelectron detector during use.

4. The system of claim 1, wherein the system is configured to assess at least one of photoelectron dose and contamination at the surface of the mask.

5. The system of claim 1, wherein the photoelectron source provides light at wavelengths between about 5 nm and about 124 nm.

6. The system of claim 1, further comprising a spectrum analzyer placed in a photoelectron collection path of the photoelectron detector, wherein the spectrum analyzer is configured to assess both the electron intensity and the electron spectra of the photoelectrons emitted from the surface of the mask.

7. A method for assessing contamination on one or more photolithography masks, comprising:
    providing a photolithography mask to a mask defect inspection stage;
    providing an inspection beam of light to the mask from a photoelectron source;
    inspecting the mask using the inspection beam of light;
    collecting photoelectrons emitted from a surface of the mask using a photoelectron detector, wherein the photoelectrons are created by impingement of the inspection beam on the surface of the mask, and wherein the photoelectron detector is located outside an optical path between the photoelectron source and the mask defect inspection stage, the optical path being used for inspection of the mask;
    biasing the surface of the mask at a first voltage;
    biasing a biasing electrode located between the mask and a scintillator of the photoelectron detector at a second voltage, wherein the second voltage is a positive potential and the first voltage has a negative potential relative to the second voltage;
    assessing both electron intensity and electron spectra of the collected photoelectrons emitted from the surface of the mask; and
    assessing, using a processor on the photoelectron detector, radiation dose, contamination level, and contamination species on the mask from the assessed electron intensity and electron spectra.

8. The method of claim 7, wherein the photoelectron detector is located a distance from the photoelectron source that inhibits the photoelectron detector causing mechanical interference with the photoelectron source.

9. The method of claim 7, further comprising introducing a time delay between emission of the inspection beam from the photoelectron source and collection of the photoelectrons by the photoelectron detector.

10. The method of claim 7, wherein the inspection beam is an inspection beam for wavelengths between about 5 nm and about 124 nm.

11. A photoelectron emission mapping system for extreme ultraviolet (EUV) mirrors, comprising:
    a mirror for use at wavelengths between about 5 nm and about 124 nm;

an EUV photoelectron source that provides light at wavelengths between about 5 nm and about 124 nm;

a photoelectron detector located to the side of the mirror, the photoelectron detector being to the side of the mirror, the photoelectron detector comprising a scintillator, wherein the photoelectron detector is configured to detect photoelectrons emitted from a surface of the mirror when light from the photoelectron source impinges on the mirror, and wherein the photoelectron detector is configured to assess both electron intensity and electron spectra of the photoelectrons emitted from the surface of the mirror, the photoelectron detector comprising a processor configured to assess radiation dose, contamination level, and contamination species on the mirror using the assessed electron intensity and electron spectra of the photoelectrons; and a biasing electrode between the mask and the scintillator;

wherein the surface of the mirror is biased at a first voltage during use and the biasing electrode is biased at a second voltage during use, wherein the second voltage is a positive potental, and wherein the first voltage has a negative potential relative to the second voltage.

12. The system of claim 11, further comprising fiber optics used to introduce a time delay between emission of light from the photoelectron source and detection of photoelectrons by the photoelectron detector during use.

13. The system of claim 11, wherein the scintillator has a voltage larger than the voltage of the biasing electrode during use to accelerate photoelectrons towards the scintillator.

14. The system of claim 11, wherein the photoelectron source is used for mask inspection or mask photolithography.

15. The system of claim 11, further comprising a spectrum analzyer placed in a photoelectron collection path of the photoelectron detector, wherein the spectrum analyzer is configured to assess both the electron intensity and the electron spectra of the photoelectrons emitted from the surface of the mirror.

16. A method for assessing contamination on one or more extreme ultraviolet (EUV) mirrors, comprising:

providing an EUV beam to an EUV mirror from a photoelectron source that provides light at wavelengths between about 5 nm and about 124 nm;

inspecting the mirror using the EUV beam;

collecting photoelectrons emitted from a surface of the mirror using a photoelectron detector, wherein the photoelectrons are created by impingement of the EUV beam on the surface of the mirror, wherein the photoelectron detector is located to the side of the mirror, and wherein the photoelectron detector is located outside an optical path between the photoelectron source and the mirror, the optical path being used for inspection of the mirror;

biasing the surface of the mirror at a first voltage;

biasing a biasing electrode located between the mask and a scintillator of the photoelectron detector at a second voltage, wherein the second voltage is a positive potential and the first voltage has a negative potential relative to the second voltage;

assessing both electron intensity and electron spectra of the collected photoelectrons emitted from the surface of the mirror; and assessing, using a processor on the photoelectron detector, radiation dose, contamination level, and contamination species on the mirror from the assessed electron intensity and electron spectra.

17. The method of claim 16, further comprising introducing a time delay between emission of the inspection beam from the photoelectron source and collection of the photoelectrons by the photoelectron detector.

18. The method of claim 16, further comprising providing a biasing voltage to accelerate the photoelectrons towards the photoelectron detector.

\* \* \* \* \*